(12) United States Patent
Oka et al.

(10) Patent No.: US 7,773,210 B2
(45) Date of Patent: Aug. 10, 2010

(54) APPEARANCE INSPECTION APPARATUS

(75) Inventors: Kenji Oka, Hitachinaka (JP); Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/482,479

(22) Filed: Jun. 11, 2009

(65) Prior Publication Data
US 2009/0244529 A1 Oct. 1, 2009

Related U.S. Application Data

(63) Continuation of application No. 11/830,320, filed on Jul. 30, 2007, now Pat. No. 7,557,911.

(30) Foreign Application Priority Data

Jul. 31, 2006 (JP) .............................. 2006-207780

(51) Int. Cl.
*G01N 21/00* (2006.01)
(52) U.S. Cl. .................................. 356/237.1; 356/237.2

(58) Field of Classification Search .... 356/237.1–237.5
See application file for complete search history.

(56) References Cited

U.S. PATENT DOCUMENTS 6,762,831 B2 7/2004 Shibata et al.
7,505,125 B2 3/2009 Andrews et al.

FOREIGN PATENT DOCUMENTS

JP 09-304289 11/1997

*Primary Examiner*—Michael P Stafira
(74) *Attorney, Agent, or Firm*—Crowell & Moring LLP

(57) ABSTRACT

An appearance inspection apparatus analyzes a difference in detection characteristics of detection signals obtained by detectors to flexibly meet various inspection purposes without changing a circuit or software. The apparatus includes a signal synthesizing section that synthesizes detection signals from the detectors in accordance with a set condition. An input operating section sets a synthesizing condition of the detection signal by the signal synthesizing section, and an information display section displays a synthesizing map structured based on a synthesized signal which is synthesized by the signal synthesizing section in accordance with a condition set by the input operating section.

11 Claims, 5 Drawing Sheets

CALCULATION RESULT 202

APPEARANCE INSPECTION APPARATUS

CROSS REFERENCE TO RELATED APPLICATION

This application is a continuing application of U.S. application Ser. No. 11/830,320, filed Jul. 30, 2007, which claims priority under 35 U.S.C. §119 to Japanese Patent Application No. 2006-207780, filed Jul. 31, 2006, the entire disclosure of which are herein expressly incorporated by reference.

BACKGROUND OF THE INVENTION

1. Field of the Invention

The present invention relates to an appearance inspection apparatus for detecting minute foreign matters or defects on a semiconductor wafer.

2. Description of the Related Art

There is a technique in which in an appearance inspection apparatus for inspecting a defect on a surface of a wafer, COP (Crystal Originated Particles) defects are discriminated using a scattered light detecting section (which will appropriately be described as a multi-sensor, hereinafter) having a plurality of detectors disposed around an illumination light spot on a sample such that orientations and elevation angles thereof are different from each other, and utilizing a difference in detection characteristics caused by a difference of an elevation angle of the detectors (see Japanese Patent Application Laid-open No. 9-304289 and the like).

SUMMARY OF THE INVENTION

According to the technique disclosed in Japanese Patent Application Laid-open No. 9-304289, detection signals from each detectors of the multi-sensor are synthesized in accordance with software which is previously stored so as to discriminate the COP defects, and an observation image of a wafer in which mainly COP defects are reflected on a wafer map is structured based on the synthesized signal. However, when it is desired to obtain an observation image of defects having different detection characteristics other than COP defects such as foreign matters adhered on the wafer surface and flaws on the wafer surface, it is necessary to recompose a signal processing circuit of a detection signal from each detector and to re-structure the software.

To that end, there is required a series of operations such as a: a result of detection of the multi-sensor is compared with an inspection defect of the same wafer by another inspection apparatus and they are analyzed off-line, b: software suitable for discriminating a new inspection subject (flaw on a wafer surface for example) is prepared based on the analysis result, and c: the prepared software is installed in the original appearance inspection apparatus. With this, much labor and much time are required in some cases.

It is an object of the present invention to provide an appearance inspection apparatus capable of analyzing a difference in detection characteristics of detection signals obtained by a plurality of detectors, and capable of flexibly meeting various inspection purposes without changing a circuit or software.

To achieve the above object, a first aspect of the present invention provides an appearance inspection apparatus including a sample stage for supporting a sample, an illumination light source for irradiating the sample on the sample stage with illumination light, a plurality of detectors which are disposed at different positions from each other with respect to an illumination light spot of the illumination light source, and which detect scattered light generated from a surface of the sample when illumination light is emitted from the illumination light source, a signal synthesizing section which synthesizes detection signals from the plurality of detectors in accordance with a set condition, a condition setting section for setting a synthesizing condition of the detection signal by the signal synthesizing section, and a display section for displaying a synthesized sample image structured based on a synthesized signal which is synthesized by the signal synthesizing section in accordance with a condition set by the condition setting section.

According to a second aspect, in the first aspect, the display section displays a plurality of individual sample images structured based on detection signals from the plurality of detectors.

According to a third aspect, in the second aspect, the plurality of individual sample images are displayed on the same screen as that of the synthesized sample image.

According to a fourth aspect, in the first aspect, when a setting of the synthesizing condition of the detection signal is changed by the condition setting section, the synthesized sample image is newly structured in accordance with the changed synthesizing condition, and the change in the synthesizing condition is reflected.

According to a fifth aspect, in the first aspect, the display section displays a list of detection data by the plurality of detectors.

According to a sixth aspect, in the first aspect, the synthesizing condition of the detection signals of the plurality of detectors can be set by a GUI operation on a display screen of the display section.

According to the present invention, it is possible to analyze a difference in detection characteristics of detection signals obtained by a plurality of detectors on the apparatus, and capable of flexibly meeting various inspection purposes without changing a circuit or software.

DESCRIPTION OF THE PREFERRED EMBODIMENTS

Figure 1:
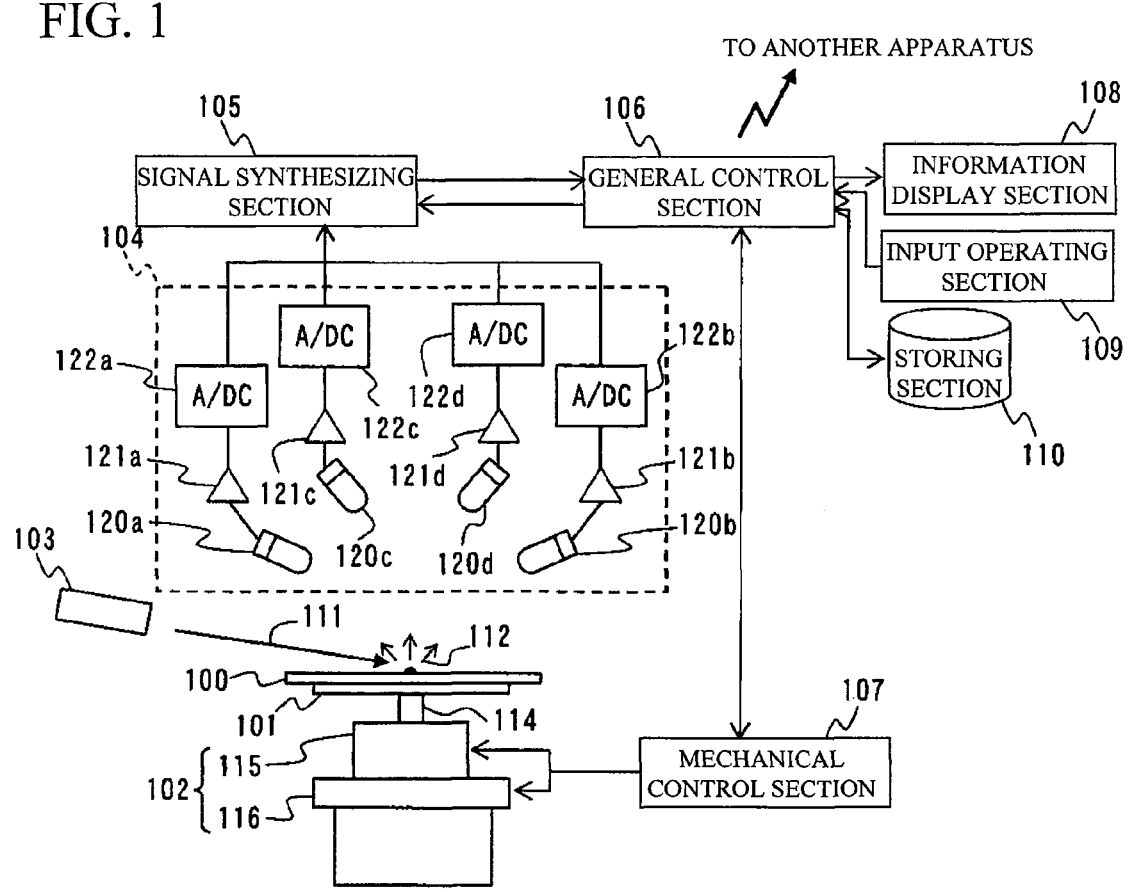
FIG. 1 is a conceptional diagram of an appearance inspection apparatus according to an embodiment of the present invention.

An embodiment of the present invention will be explained using the drawings below. FIG. 1 is a conceptional diagram of an appearance inspection apparatus according to the embodiment of the invention. As shown in FIG. 1, the appearance inspection apparatus includes a sample stage 101, a stage driving section 102, an illumination light source 103, a scattered light detecting section 104, a signal synthesizing section 105, a general control section 106, a mechanical control section 107, an information display section 108, an input operating section 109, a storing section 110 and the like.

The sample stage 101 supports a sample 100 of a wafer or the like placed on the sample stage 101. The stage driving section 102 drives the sample stage 101 such that a fixed point (spot) is irradiated with illumination light 111 from the illumination light source 103 and the illumination light 111 scans on the sample 100.

The stage driving section 102 includes a rotation driving section 115 which rotates the sample stage 101 around a rotation shaft 114, and a slide driving section 116 which moves the sample stage 101 in the radial direction. When the sample 100 on the sample stage 101 is irradiated with the illumination light 111 by the illumination light source 103, the rotation driving section 115 rotates the sample stage 101 and the slide driving section 116 moves the sample stage 101 in the radial direction so that the illumination light 111 spirally scans on the sample 100 relatively.

The scattered light detecting section 104 includes a plurality of detectors 120a to 120d having different positions with respect to the spot of the illumination light 111. In FIG. 1, four detectors are shown in total, i.e., the detectors 120a and 120b disposed at the low angle positions and the detectors 120c and 120d disposed at the high angle positions, but the number of detectors is not limited only if two or more detectors are disposed such that at least one of the azimuth angle from the illumination light spot and the elevation angle is different. The detectors 120a to 120d detect the scattered light 112 generated from the surface of the sample 100 when the illumination light 111 is emitted from the illumination light source 103. A detection signal (which will appropriately be described as a defect signal) of a defect which is a high frequency component and Hayes signal which is a low frequency component are included in outputs of the detectors 120a to 120d.

In the scattered light detecting section 104, amplifiers 121a to 121d and A/D converters 122a to 122d are respectively connected to the detectors 120a to 120d. Detection signals from the detectors 120a to 120d are amplified through the amplifiers 121a to 121d, and digitized through the A/D converters 122a to 122d.

The signal synthesizing section 105 synthesizes the digitized detection signals from the detectors 120a to 120d in accordance with a designated calculation condition (program). The later-described calculation condition of the synthesized signal in the signal synthesizing section 105 is not predetermined fixed condition, and the calculation condition can appropriately designated and changed by an operator using the input operating section 109. Data of the synthesized signal which is synthesized by the signal synthesizing section 105 is output to the storing section 110 and stored therein together with data of detection signals of the detectors 120a to 120d which are bases of the synthesized signal. Examples of these data sets are positions (XY coordinates) and sizes of individual detected defects. These data sets may be output to an inspection apparatus using an electron microscope or other inspection apparatuses and producing apparatuses through a network.

The general control section 106 processes signals concerning display, input and output of information required for steps of operations (setting of inspection condition, display of results, analysis and designation of calculation equation), and control the entire apparatus. For example, the general control section 106 outputs a command signal to the mechanical control section 107 based on an operation signal from the input operating section 109 and a corresponding program stored in the storing section 110, and changes the calculation condition of the synthesized signal in the signal synthesizing section 105. The mechanical control section 107 receives the command signal from the general control section 106 and controls driving mechanisms such as the rotation driving section 115 and the slide driving section 116. The general control section 106 also outputs, to the storing section 110, a synthesized signal which is input through the signal synthesizing section 105 and a detection signals from the detectors 120a to 120d, and allows the storing section 110 to store these signals, and produces a display signal to the information display section 108 based on these signals, and display an image on the information display section 108.

The input operating section 109 is for instructing input operation of a synthesizing condition of a detection signal by the signal synthesizing section 105 and operation of each apparatus.

The information display section 108 displays a sample image (called "synthesized sample image", hereinafter for convenience sake) structured based on a synthesized signal synthesized by the signal synthesizing section 105 in accordance with a condition designated by the input operating section 109, a plurality of sample images (called "individual sample images", hereinafter for convenience sake) corresponding to individual detectors structured based on a detection signal from a corresponding detector, and detection data and a detection condition (recipe). For example, the information display section 108 displays a result of inspection after the inspection is completed, and displays a synthesized sample images and an individual sample images on the same screen at the time of analysis. The synthesized sample images and the individual sample images may be displayed in a switching manner.

The storing section 110 stores, therein, programs required for various control and calculations, constants, inspection results (data of synthesized sample images and individual sample images), and a synthesizing condition which is set by the input operating section 109. Data of the individual sample image of each of the detectors 120a to 120d is stored together with address information of the detectors.

As described above, the synthesis of a detection signal by the signal synthesizing section 105 is executed in accordance with a condition which is set by an operator using the input operating section 109. This setting can always be changed by inputting operation of the input operating section 109.

Figure 2:
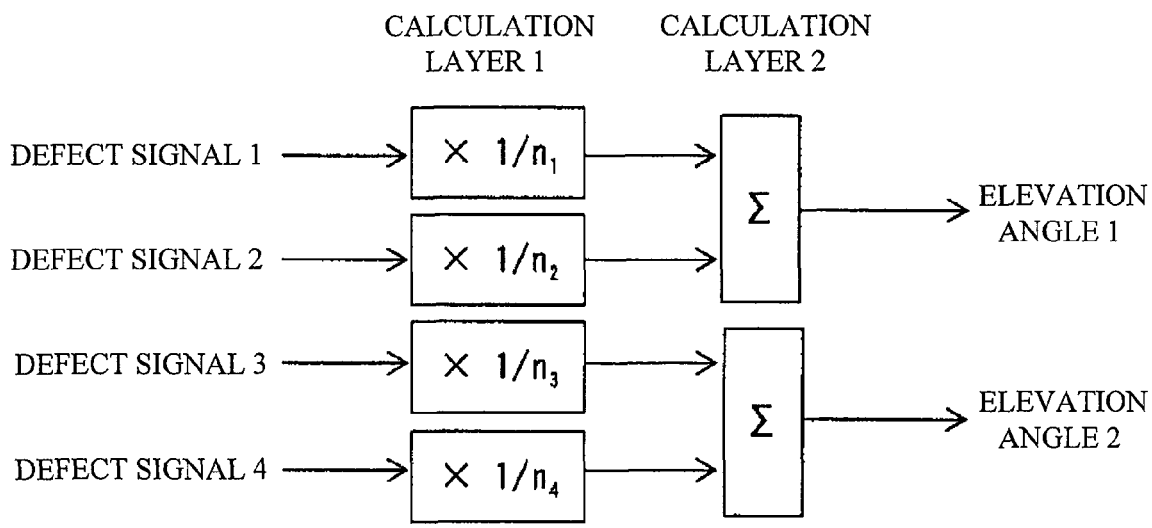
FIG. 2 is a diagram showing one example of a synthesizing condition of a detection signal.
Figure 3:
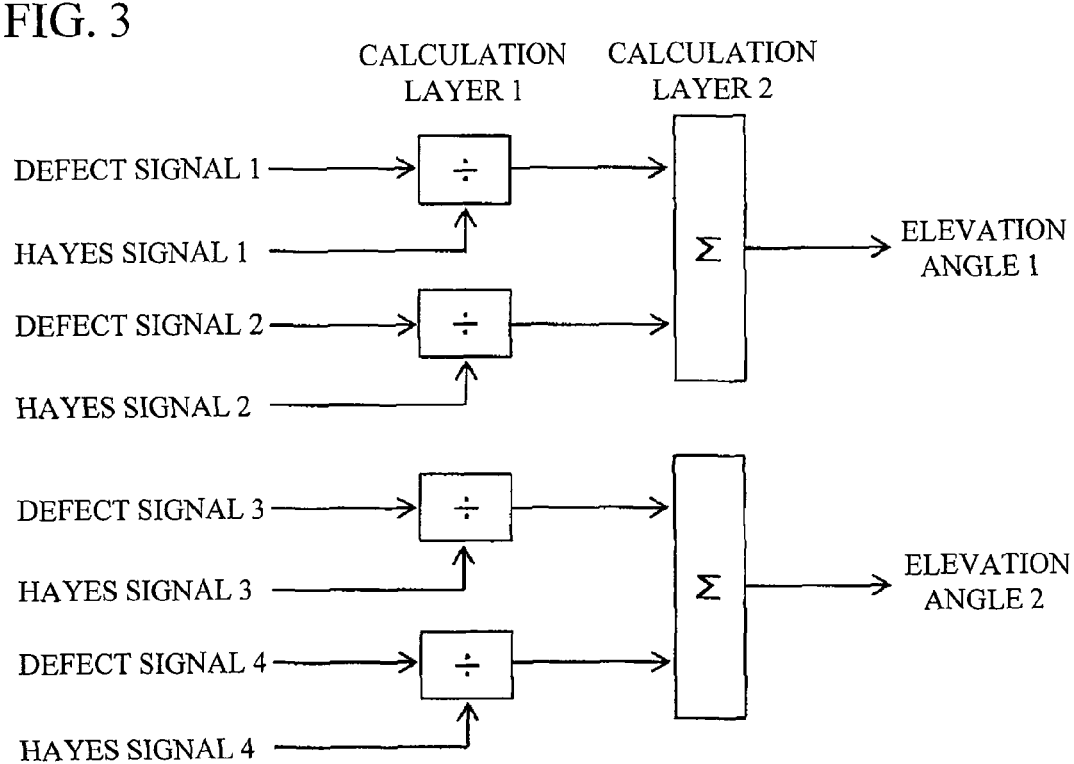
FIG. 3 is a diagram showing one example of the synthesizing condition of the detection signal.
Figure 4:
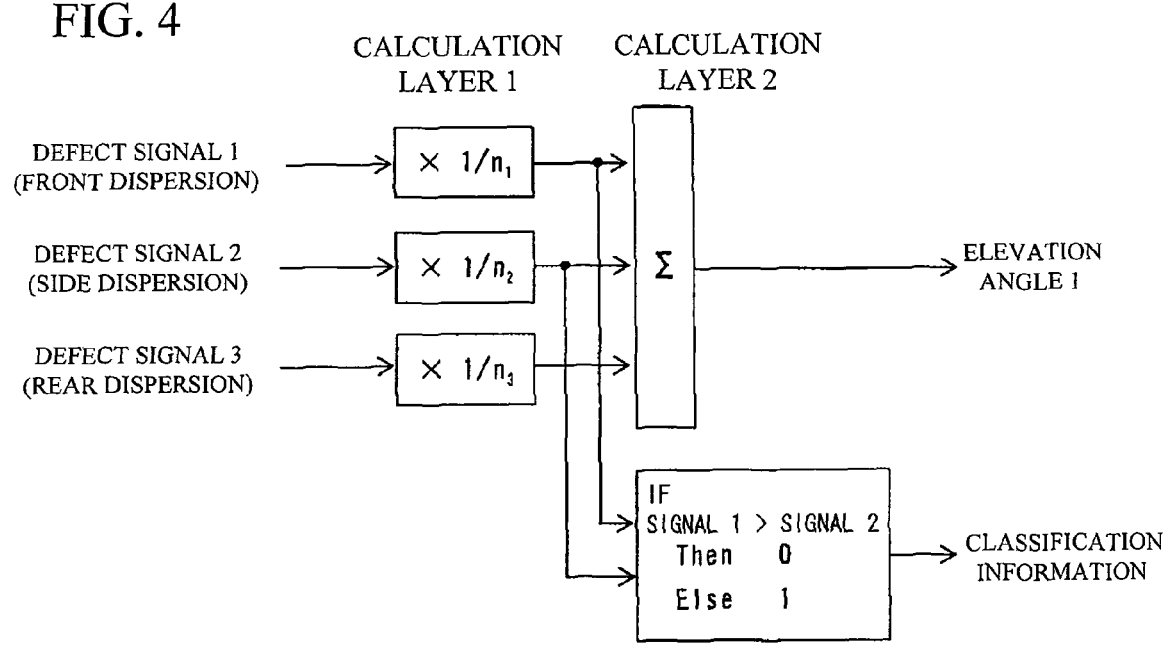
FIG. 4 is a diagram showing one example of the synthesizing condition of the detection signal.

FIGS. 2 to 4 show several examples of the synthesizing condition of a detection signal. FIG. 2 shows one useful example to suppress a noise in a specific orientation, and to enhance a defect detection S/N. Based on the fact that the detection signal has orientational properties, a noise level is optimized in accordance with a inspection purpose by making it possible to freely set a constant which is to be multiplied by the detection signal of the each detectors, because of differences in the orientations of the detectors from the illumination light spot.

In the example shown in FIG. 2, when synthesizing defect signals 1 and 2 detected by the detectors 120a and 120b at the low angle (elevation angle 1), a signal obtained by multiplying the defect signal 1 by $1/n_1$, and a signal obtained by multiplying the defect signal 2 by $1/n_2$ are added. At that time, $1/n_1$ and $1/n_2$ are arbitrary numeric values which are input by an operator using the input operating section 109 while taking, into consideration, positions of the detectors 120a and 120b with respect to the illumination light spot in accordance with the inspection purpose. Similarly, when synthesizing defect signals 3 and 4 detected by the detectors 120c and 120d at the high angle (elevation angle 2), a signal obtained by multiplying the defect signal 3 by $1/n_3$, and a signal obtained by multiplying the defect signal 4 by $1/n_4$ are added. Here also, $1/n_3$ and $1/n_4$ are arbitrary numeric values which are input by an operator using the input operating section 109 while taking, into consideration, positions of the detectors 120c and 120d with respect to the illumination light spot.

In the example shown in FIG. 3, when synthesizing the defect signals 1 and 2 detected by the detectors 120a and 120b at the low angle (elevation angle 1), a signal obtained by dividing the defect signal 1 by a Hayes signal 1 detected by the detector 120a, and a signal obtained by dividing the defect signal 2 by a Hayes signal 2 detected by the detector 120b are added. Similarly, when synthesizing defect signals 3 and 4 detected by the detectors 120c and 120d at the high angle (elevation angle 2), a signal obtained by dividing the defect signal 3 by a Hayes signal 3 detected by the detector 120c, and a signal obtained by dividing the defect signal 4 by a Hayes signal 4 detected by the detector 120d are added. In the case of this embodiment, it is possible to easily change the synthesizing condition shown in FIG. 2 to the synthesizing condition for enhancing S/N using the Hayes signals shown in FIG. 3 by means of the input operating section 109.

FIG. 4 shows one example for obtaining classification information of the detection signals. In FIG. 4, when synthesizing the defect signals 1 to 3 from the detectors at the elevation angle 1 located in a front direction of, in a side direction of and in a rear direction of the illumination light spot, the detection signals 1 to 3 are multiplied by arbitrary coefficients and added like the example shown in FIG. 2. This synthesizing condition is not limited, and may be replaced by the synthesizing condition shown in FIG. 3.

At that time, a correlation between detection signals detected by detectors at various positions generated by sizes of the signals and inspection purposes (flaw, foreign matter, COP and the like) is taken conditions, and a result obtained by such a condition may be obtained as classification information (any attribute signal which can be identified) of a defect. In the example shown in FIG. 4, sizes of the defect signal 1 which is multiplied by $1/n_1$ and the defect signal 2 which is multiplied by $1/n_2$ are compared with each other, and if the defect signal 1 is greater than the defect signal 2, an attribute identified by 0 (zero) is given to information such as a size and a position of a detected defect and a detector address as the classification information, and if the defect signal 1 is smaller than the defect signal 2, an attribute identified by 1 is given. That is, kinds of defects are identified by the attribute information (0 or 1) incidental to the detected defect information. In this example, a defect is classified by means of a ratio between scattered light (scattered light dispersed forward) detected by a detector disposed in the front direction of the illumination light spot and scattered light (scattered light dispersed sideward) detected by a detector disposed in the side direction of the illumination light spot.

By classifying a defect in this manner, each kind of defect after classification can have precise sensitive curve, and this also enhance the detection precision of size of defect.

Figure 5:
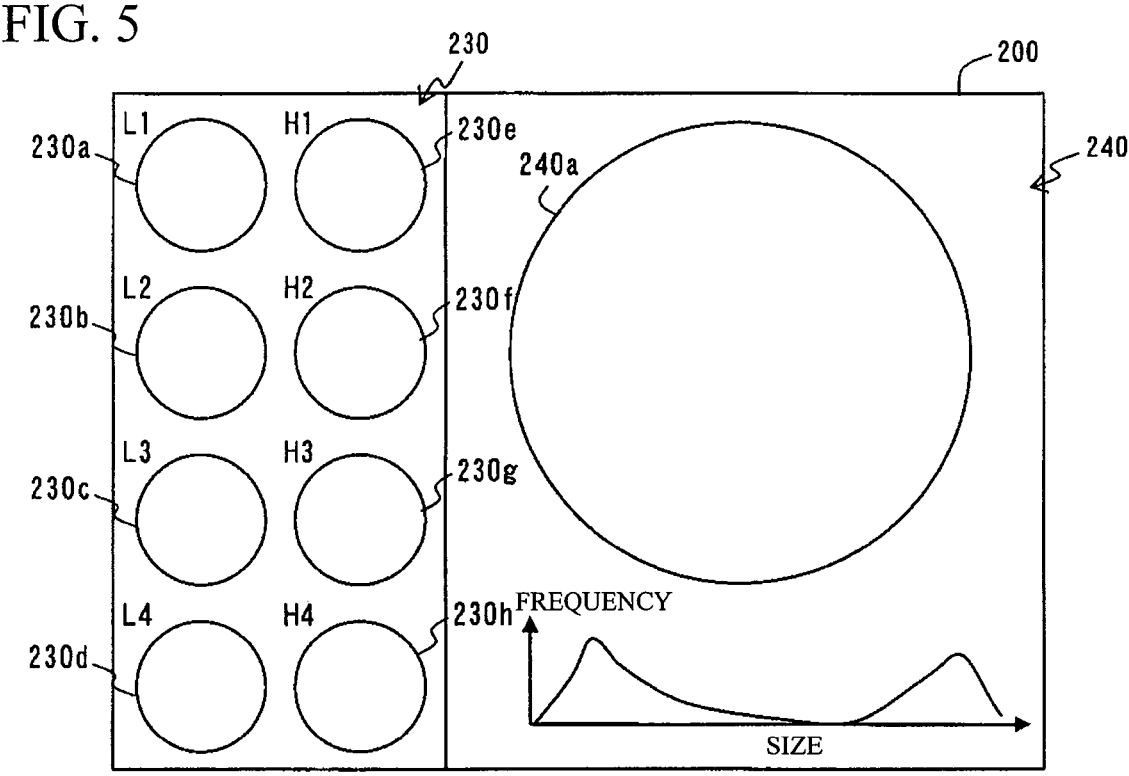
FIG. 5 is a diagram showing one example of an analysis screen displayed on an information display section.

FIG. 5 shows one example of an analysis screen displayed on the information display section 108. As shown in FIG. 5, a display region 230 of total eight individual maps 230a to 230h and a display region 240 of an enlarged map 240a on which selected one of the individual maps 230a to 230h is displayed in an enlarged scale are disposed in the analysis screen 200. In the example shown in FIG. 5, the scattered light detecting section 104 has total eight detectors comprising detectors L1 to L4 at low angle disposed in four orientations, and detectors H1 to H4 at high angle disposed in four orientations.

The individual sample image is displayed on the individual map 230a in such a form that a defect detected by the detector L1 at corresponding low angle is superposed on a wafer map. Similarly, individual sample images detected by corresponding detectors L2 to L4 and H1 to H4 are displayed on the individual maps 230b to 230h. The individual maps 230a to 230h may be displayed at locations corresponding to the actual layout of the detectors L1 to L4 and H1 to H4.

On the enlarged map 240a, any one of the individual maps 230a to 230h selected by an inputting operation using the input operating section 109 or a touching operation of the individual maps 230a to 230h. A histogram having a size of a defect displayed on the enlarged map 240a is displayed in a lower range of the enlarged map 240a in the analysis screen 200.

With this, the enlarged map 240a and the histogram can sequentially be checked for each of the individual maps 230a to 230h, defect distribution of each size can be checked, and a range difference in a noise level can be determined. If the individual maps 230a to 230h are displayed on the analysis screen 200 in the form of a list, dependency tendency of distribution of defect size toward the detector orientation can also be checked.

Figure 6:
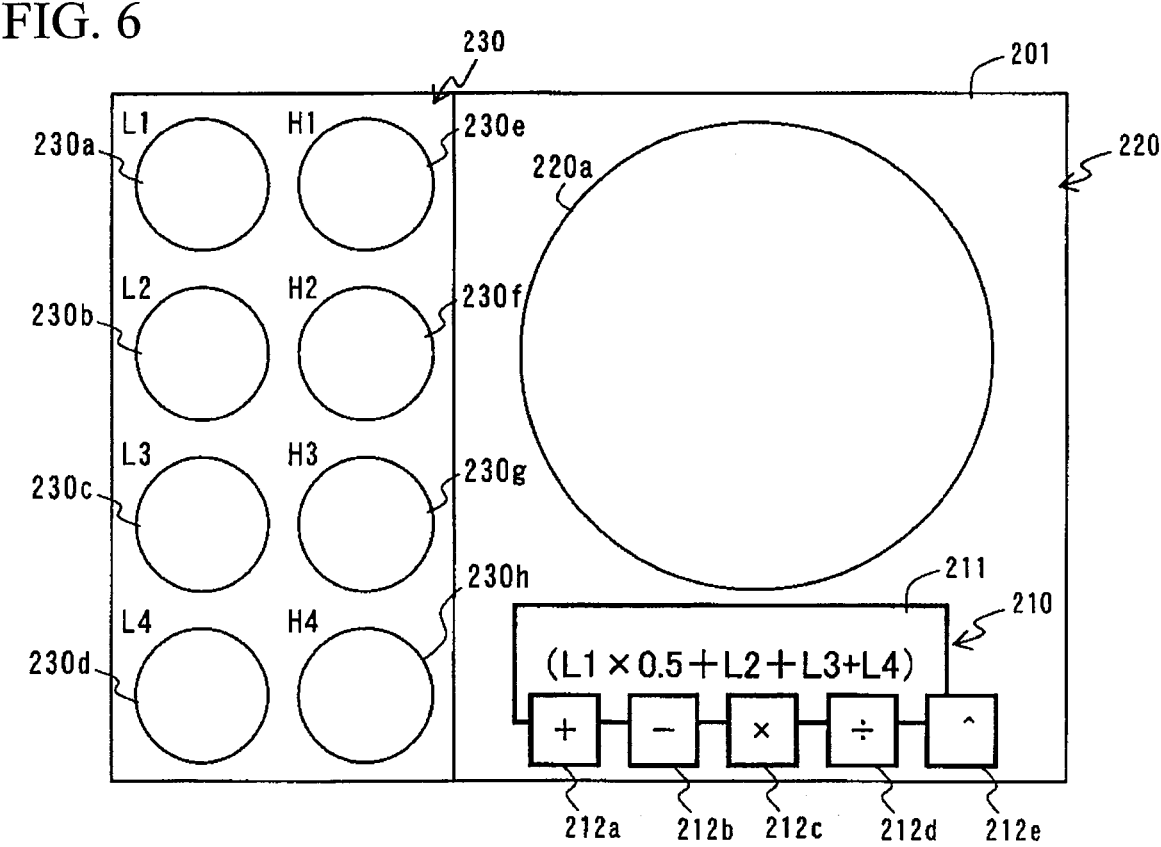
FIG. 6 is a diagram showing one example of a simulation screen displayed on the information display section.

FIG. 6 shows one example of a simulation screen displayed on the information display section 108. The simulation screen 201 shown in FIG. 6 is a screen in which display is shifted by an analysis screen 200 by a touching operation of a display switching button (not shown) provided on the analysis screen 200 or an operation using an input operating section 109. The simulation screen 201 may be provided with the display switching button (not shown) to the analysis screen 200, and the display may be shifted to the analysis screen 200 by the touching operation of the display switching button or the operation using the input operating section 109.

A condition setting region 210 for setting a synthesizing condition (calculation equation) of a detection signal, and a simulation region 220 where a synthesizing map (calculation result) 220a by a synthesized signal based on the synthesizing condition set in the condition setting region 210 are disposed in the simulation screen 201 in addition to the display region 230 of the individual maps 230a to 230h. The synthesizing map 220a may be displayed on the enlarged map 240a of the analysis screen 200.

The condition setting region 210 is provided with a display region 211 of the synthesizing condition, and a synthesizing condition which is set by an inputting operation using the input operating section 109 or a touching operation of various operator buttons 212a to 212e and the individual maps 230a to 230h provided in the condition setting region 210 is displayed in the condition setting region 210. In the example shown in FIG. 6, a case where a detection signal of the detector L1 is multiplied by a coefficient 0.5 (=½) and a result thereof is added to the detection signal is shown in the display region 211 as a synthesizing condition of signals of the detectors L1 to L4 at low angle. In this case, the inspection purpose and the orientations of the detectors are taken into consideration, and an operator inputs a synthesizing condition for weakening a detection signal of the detector L1 located in a specific orientation as compared with other detectors L2 to L4.

In addition to operators such as "+ (addition)", "− (subtraction)", "× (multiplication)", "÷ (division)" and "^ (exponentiation)" with respect to arbitrary two inputs and constant, operators of condition branch, a total (Σ) of a plurality of values are appropriately combined, and one of a plurality of calculation layers as shown in FIGS. 2 to 4 are set, and a synthesizing condition of a detection signal is set. When values obtained by multiplying detection signals of the detectors by coefficients are summed up, it is conceived that slider switches (scroll bars) are provided near the individual maps 230a to 230h so that coefficients with respect to the detection signals can be changed by operating the slider switches. In this embodiment, the setting of the synthesizing condition of the detection signal can be changed very easily on the screen of the information display section 108 by the GUI operation.

A synthesized sample image is displayed on the synthesizing map 220a in accordance with the display region 211 shown in FIG. 6 or a synthesizing condition shown FIGS. 2 to 4 in such a form that detection signals of the detectors are synthesized by the signal synthesizing section 105 to obtain a synthesized signal, and a defect image produced based on the sample stage is superposed on a wafer map. If the synthesizing condition of the detection signals of the detectors is changed by the above-described operation, a synthesized sample image structured by a synthesized signal in accordance with a synthesizing condition after change is reflected to the synthesizing map 220a, and a result of detection of the inspection apparatus by the change of the synthesizing condition is always simulated by the simulation region 220.

An operator arbitrarily sets a synthesizing condition of a signal while seeing detection signals of the detectors by the inspection purpose and the individual map. With this, it is possible to customize the inspection apparatus and to optimize an inspection result in accordance with the inspection purpose.

Figure 7:
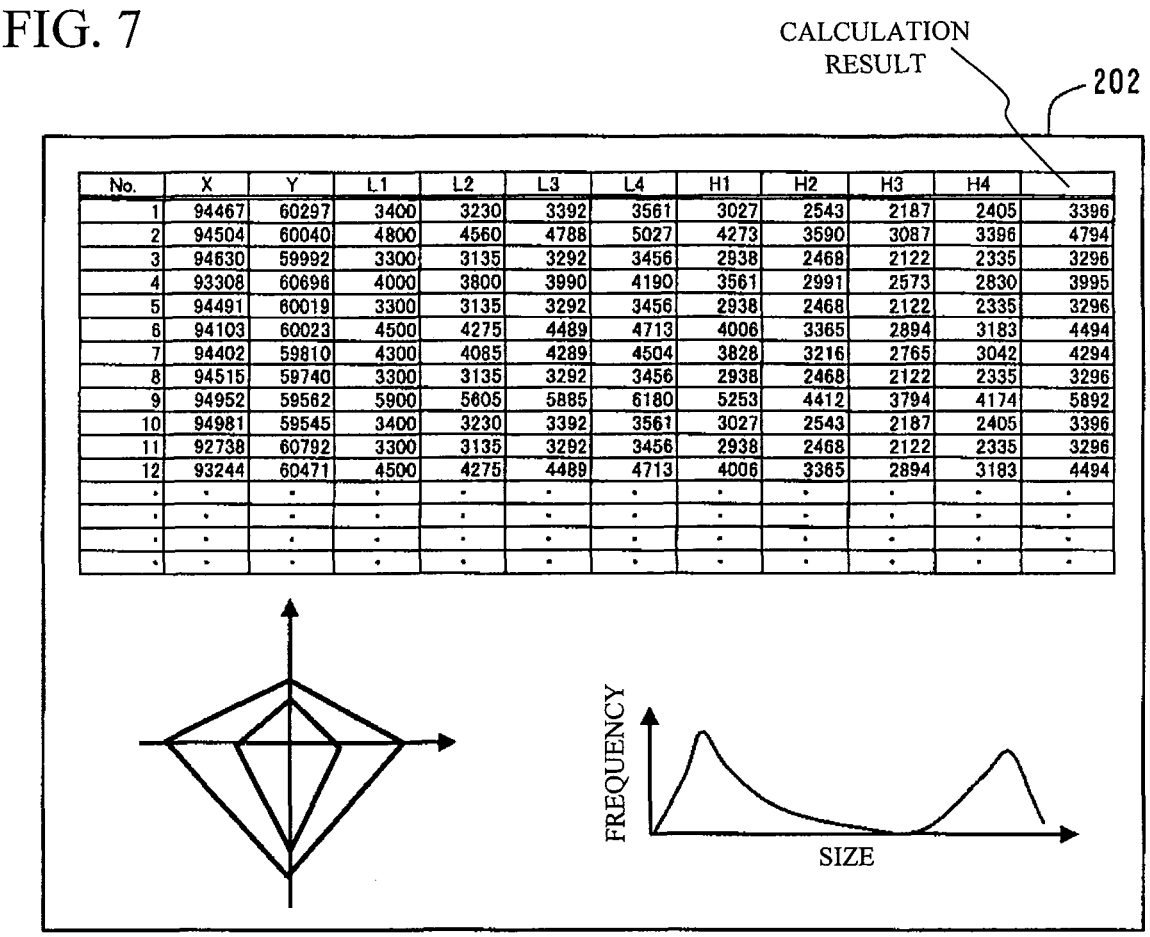
FIG. 7 is a diagram showing one example of a data list display screen displayed on the information display section.

FIG. 7 shows one example of a data list display screen displayed on the information display section 108. A coordinate position (X, Y) on a wafer, detection sizes by the detectors L1 to L4 and detection size by synthesized signal under a set synthesizing condition are displayed on the data list display screen 202 with respect to defects (Nos. 1, 2 . . . ) in a form of a list. Information from which distribution and tendency of data can visually be discriminated such as a histogram of size of a detected defect and a chart are also displayed in addition to the list.

The data list display screen 202 can be switched to a previous analysis screen 200 and the simulation screen 201 by operating the display switching button (object on the screen 202) (not shown) or operation by the input operating section 109.

Figure 8:
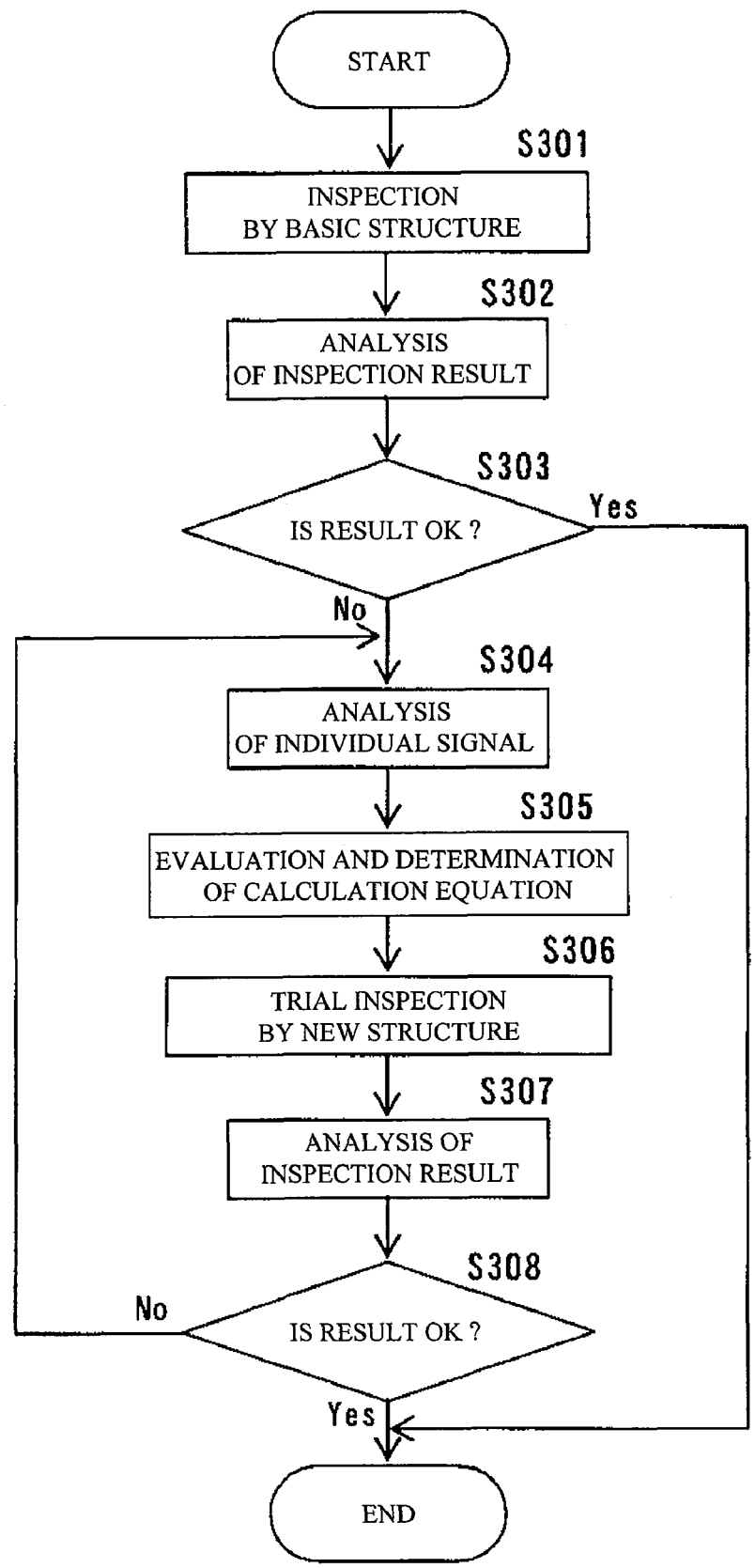
FIG. 8 is a flowchart showing setting procedure of a synthesizing condition of a detection signal using the appearance inspection apparatus according to the one embodiment of the invention.

FIG. 8 is a flowchart showing setting procedure of a synthesizing condition of a detection signal using the appearance inspection apparatus having the above-described structure. When a synthesizing condition of a detection signal is to be changed in the appearance inspection apparatus of the embodiment, a wafer whose coordinates, size and kind of a defect are known to some extent in another inspection apparatus is loaded onto a sample stage 101, and a defect inspection is carried out under the current synthesizing condition (or reset synthesizing condition) (step 301). If the input operating section 109 instructs to start the inspection, illumination light from the illumination light source 103 is scanned on the rotating sample 100, and scattered light from the sample 100 is detected by each detector. The detection signal by each detector is synchronized with a position (coordinates) of the illumination light spot on the sample 100 by a motion signal of the sample stage 101 which instructs the mechanical control section 107, and a result of detection of each detector is stored in the storing section 110 together with defect information such as coordinates, size, detector address and a synthesized signal.

In step 302, a predetermined operation is carried out on the input operating section 109 or the information display section 108, the information display section 108 is instructed to display the analysis screen 200 of FIG. 5, and a result of the inspection is analyzed (sensitivity is checked for example). The general control section 106 which receives an operation signal from the input operating section 109 reads a detection signal and a synthesized signal of each detector stored in the storing section 110, and a display signal produced based on these information sets is output to the information display section 108. With this, the analysis screen 200 is displayed on the information display section 108. The operator checks a result of detection by each detector under the current condition by the individual maps 230a to 230h and the enlarged map 240a, the current inspection result is compared with the known defect information, and it is analyzed whether the inspection result is excellent.

In step 303, a result of the analysis and the current signal synthesizing condition meet the next inspection purpose (if the current sensitivity is sufficient in the case of sensitive optimization), it is unnecessary to change the synthesizing condition and thus, the synthesizing condition setting procedure is completed, and an inspection step of a wafer is started using the current synthesizing condition as it is. If the current signal synthesizing condition does not meet the inspection purpose (if the current sensitivity is insufficient in the case of sensitive optimization), the procedure is proceeded to synthesizing condition changing procedure in steps 304 and 305.

In step 304, the inspection purpose (kind of defect to be inspected), a position of a detector (orientation, elevation angle), defect Hayes and the like are taken into consideration, and the individual map, the enlarged map, the histogram and the like are checked on the analysis screen 200.

In step 305, display of the information display section 108 is switched to the simulation screen 201, and as results of evaluation and analysis in the analysis screen 200, a synthesizing condition meeting the inspection purpose are determined, and they are newly set in the condition setting region 210. Results of change in the synthesizing condition are sequentially reflected on the synthesizing map 220a and the individual maps 230a to 230h. In step 305, a synthesizing condition after change is output to the storing section 110 and stored therein through the general control section 106. The stored new synthesizing condition is read by the general control section 106 together with detection signals of the detectors, display data of the synthesized sample image is produced by the general control section 106 based on the new synthesizing condition, and the display data is output to the information display section 108. The validity of the synthesizing condition is evaluated by a simulation image displayed on the synthesizing map 220a, and if it is determined that the synthesizing condition is valid, the synthesizing condition is once determined.

In next step 306, a defect inspection of the same wafer is again carried out under the newly set synthesizing condition, and a result thereof is analyzed in step 307 as in the same manner as that in step 302. In step 308, in the same manner as that in step 303, if a signal synthesizing condition after change meets the inspection purpose (if the current sensitivity is sufficient in the case of sensitive optimization), it is unnecessary to change the synthesizing condition thereafter and thus, the inspection synthesizing condition setting procedure is completed, and an inspection step of a wafer is started using the current synthesizing condition as it is. If the signal synthesizing condition after change does not yet meet the inspection purpose (if the current sensitivity is insufficient in the case of sensitive optimization), the procedure is returned to step 304, and attempt is made to change the synthesizing condition again. The change in synthesizing condition and a trial inspection under the synthesizing condition after change are repeated and if an excellent inspection result is obtained, the procedure in FIG. 8 is completed.

According to this embodiment, the following effects can be obtained. When a defect such as a COP, a flaw, a foreign matter (particle) or the like on a wafer is to be inspected, in an appearance inspection apparatus having a plurality of detectors (multi-sensors) a synthesizing condition of a detection signal of each detector is set as a parameter suitable for a kind of the defect to be detected. Thus, when the inspection purpose is to be changed, it is necessary to change the parameter to optimize the sensitivity in accordance with a kind of the defect of the purpose. In this case, to change a parameter, much labor and time are required for a series of operations including evaluation of an inspection result on off-line operation, analysis, preparation of software and install of the prepared software in some cases.

According to the embodiment, a result of inspection of a defect of a wafer can be checked in the information display section 108 and after that, it is possible, on the appearance inspection apparatus, to evaluate and analyze the inspection result, to change a signal synthesizing condition by the input operating section 109, to simulate a synthesizing map after change, and to check a result of an inspection after the condition is changed. A difference in detection characteristics of detection signals obtained by a plurality of detectors is analyzed on the apparatus, and it is possible to flexibly and swiftly satisfy various inspection purposes with minimum labor without changing a circuit and software. Since multi-sensors are mounted, it is possible to discriminate differences of detection signals in accordance with orientational properties of scattered light depending on kinds of defects and with this, such a large merit can be obtained.

It is possible to arbitrarily and easily change a synthesizing condition of a detection signal. Thus, trial inspections can be repeated under various synthesizing conditions, and if a result of detection and a tendency thereof (orientation of detection signal, dependency on elevation angle and the like) are analyzed, it is possible to expect application of defects to specification of parameters for inspection and classification which could not easily be found in the appearance inspection apparatus of this kind.

What is claimed is:

1. An inspection method comprising:
   irradiating a sample with illumination light;
   detecting scattered light generated from a surface of the sample upon irradiation of the sample at a plurality of different positions with the illumination light;
   synthesizing detection signals obtained at the plurality of different positions in accordance with a preset condition; and
   displaying a synthesized sample image structured based on a synthesized signal which is synthesized in accordance with the preset condition.

2. The inspection method according to claim 1, wherein a plurality of individual sample images that are structured based on the plurality of detection signals are displayed on a screen.

3. The inspection method according to claim 2, wherein the plurality of individual sample images are displayed on the same display screen as that of the synthesized sample image.

4. The inspection method according to claim 1, wherein, when a setting of the synthesizing condition of the detection signals is changed, the synthesized sample image is newly structured in accordance with the changed synthesizing condition, and the change in the synthesizing condition is reflected.

5. The inspection method according to claim 1, wherein a list of detection data obtained at the plurality of different positions is displayed on a display screen.

6. The inspection method according to claim 1, wherein the synthesizing condition of the detection signals obtained at the plurality of different positions is settable by a GUI operation on a display screen.

7. An inspection apparatus, comprising:
   a sample stage for supporting a sample,
   an illumination light source for irradiating the sample on the sample stage with illumination light,
   a plurality of detectors disposed at different positions from each other with respect to an illumination light spot of the illumination light source, so as to detect scattered light generated from a surface of the sample upon emission of illumination light from the illumination light source,
   a signal synthesizing section configured to synthesize detection signals from the plurality of detectors in accordance with a preset condition, and
   an arbitrary setting section configured to freely set a constant to be multiplied by the detection signal of each detector.

8. The inspection apparatus according to claim 7, wherein the arbitrary setting section freely sets the constant to be multiplied by the detection signal of each detector based on differences in the orientations of the plurality of detectors from the illumination light spot.

9. The inspection apparatus according to claim 7, wherein the signal synthesizing section synthesizes the signals using a Hayes signal.

10. The inspection apparatus according to claim 7, wherein different kinds of defects are identified by attributed information incidental to detected defect information for the detection signals detected by the plurality of detectors.

11. The inspection apparatus, comprising:
    a sample stage for supporting a sample,
    an illumination light source for irradiating the sample on the sample stage with illumination light,
    a plurality of detectors which are disposed at different positions from each other with respect to an illumination light spot of the illumination light source, and which detect scattered light generated from a surface of the sample when illumination light is emitted from the illumination light source, and
    a signal synthesizing section configured to synthesize detection signals from the plurality of detectors in accordance with a preset condition,
    wherein, upon the synthesizing condition of the detection signal of each detector being changed, a synthesized sample image structured by a synthesized signal in accordance with the changed synthesizing condition is reflected to synthesizing map, and a result of detection of the inspection apparatus in accordance with the changed synthesizing condition can always be simulated.

* * * * *